United States Patent
Kiern et al.

(10) Patent No.: US 7,625,424 B2
(45) Date of Patent: Dec. 1, 2009

(54) AIR CLEANER AND SHUT-DOWN METHOD

(75) Inventors: Bruce Kiern, Gulfport, MS (US); Christopher M. Paterson, Biloxi, MS (US); John Relman Bohlen, Long Beach, MS (US)

(73) Assignee: Oreck Holdings, LLC, Cheyenne, WY (US)

( * ) Notice: Subject to any disclaimer, the term of this patent is extended or adjusted under 35 U.S.C. 154(b) by 384 days.

(21) Appl. No.: 11/500,816

(22) Filed: Aug. 8, 2006

(65) Prior Publication Data
US 2008/0034963 A1    Feb. 14, 2008

(51) Int. Cl.
*B03C 3/68* (2006.01)

(52) U.S. Cl. .................... 95/5; 95/6; 95/25; 96/20; 96/21; 96/22; 96/26; 96/63

(58) Field of Classification Search ................. 95/5, 95/6, 25; 96/20–22, 26, 63
See application file for complete search history.

(56) References Cited

U.S. PATENT DOCUMENTS

| | | | |
|---|---|---|---|
| 2,961,577 A * | 11/1960 | Thomas et al. ............... 96/21 |
| 3,745,749 A | 7/1973 | Gelfand |
| 4,335,414 A | 6/1982 | Weber |
| 4,507,131 A | 3/1985 | Fathauer et al. |
| 4,559,594 A | 12/1985 | Sears et al. |
| 4,605,424 A | 8/1986 | Johnston |
| 4,816,979 A | 3/1989 | Domann et al. |
| 4,860,149 A * | 8/1989 | Johnston ..................... 361/79 |
| 5,311,420 A * | 5/1994 | Zarfoss et al. ............... 700/28 |
| 5,456,741 A * | 10/1995 | Takahara et al. ............. 96/22 |
| 6,056,808 A | 5/2000 | Krause |
| 6,115,230 A | 9/2000 | Voigts et al. |
| 6,616,736 B2 * | 9/2003 | Massey et al. ............... 96/25 |
| 6,951,582 B1 * | 10/2005 | Tsai et al. ................... 96/18 |
| 7,351,274 B2 * | 4/2008 | Helt et al. .................... 95/2 |
| 2004/0004797 A1 | 1/2004 | Krichtafovitch et al. |
| 2004/0251124 A1 | 12/2004 | Lau |
| 2007/0039462 A1 * | 2/2007 | Helt et al. .................... 95/6 |
| 2008/0011162 A1 * | 1/2008 | Bohlen ........................ 96/22 |

FOREIGN PATENT DOCUMENTS

GB          2096845 A  * 10/1982 ................. 96/21

* cited by examiner

*Primary Examiner*—Richard L Chiesa
(74) *Attorney, Agent, or Firm*—Winston & Strawn LLP; Richard P. Gilly

(57) ABSTRACT

An air cleaner is provided according to an embodiment of the invention. The air cleaner includes a high voltage power supply configured to provide a high voltage to a collector cell and a shut-down circuit coupled to the high voltage power supply. The shut-down circuit is configured to monitor an electrical current supplied to the collector cell, remove electrical power to the collector cell if the electrical current exceeds a predetermined cell current threshold for a predetermined time period, and generate an indication if the electrical power is removed from the collector cell.

17 Claims, 6 Drawing Sheets

AIR CLEANER AND SHUT-DOWN METHOD

TECHNICAL FIELD

The present invention relates to an air cleaner and shut-down method

BACKGROUND OF THE INVENTION

Air cleaners are widely used in home and office settings for cleaning the air. An air cleaner can filter the air in order to remove airborne contaminants. An air cleaner can therefore include any type of mechanical filter element comprising a mesh, a weave, a foam, etc. An air cleaner can further include electrical air cleaning components, such as a collector cell that removes dirt and debris from the airflow of the air cleaner. A collector cell can include an ionizer and/or an electrostatic precipitator.

The collector cell of an air cleaner operates at very high voltages, typically in thousands of volts. The high operational voltage level of a collector cell can result in arcing or shorting during operation. The arcing or shorting can result from excessive accumulation of dirt and debris in the collector cell over operation, such as insects between the charge and ground components, for example. The arcing or shorting can result from fluids or high levels of moisture in the collector cell. For example, water or cleaning fluids can remain in the collector cell after a cleaning operation.

The arcing or shorting over very short periods of time generates loud and annoying noises, at the very least. The arcing or shorting can cause damage to electrical components of the air cleaner. In more severe cases, the arcing or shorting can present a danger of fire or electrical shock. Therefore, it is highly undesirable that the collector cell be allowed to continuously or repeatedly arc or short during operation.

In the prior art, a typical approach in an air cleaner is to detect a drop in electrical current or voltage and temporarily shut down the collector cell. The electrical power is then ramped back up, on the theory that the cause of the arc or short has probably traveled out of the collector cell or has been otherwise removed.

Drawbacks exist in the prior art. The electrical power can be ramped back up even though the cause of the arcing or shorting has not been removed. Because the power circuitry in the prior art performs this ramping up at a fixed time after shutting down, the user or operator may not be aware of the arcing or shorting. Repeated arcing or shorting will consume excessive electrical power. Moreover, repeated arcing or shorting can present a danger to the device and surroundings if excessive electrical power is consumed.

SUMMARY OF THE INVENTION

An air cleaner is provided according to an embodiment of the invention. The air cleaner comprises a high voltage power supply configured to provide a high voltage to a collector cell and a shut-down circuit coupled to the high voltage power supply. The shut-down circuit is configured to monitor an electrical current supplied to the collector cell, remove electrical power to the collector cell if the electrical current exceeds a predetermined cell current threshold for a predetermined time period, and generate an indication if the electrical power is removed from the collector cell.

A shut-down method for a collector cell of an air cleaner is provided according to an embodiment of the invention. The method comprises monitoring an electrical current supplied to the collector cell, removing electrical power to the collector cell if the electrical current exceeds a predetermined cell current threshold for a predetermined time period, and generating an indication if the electrical power is removed from the collector cell.

A shut-down method for a collector cell of an air cleaner is provided according to an embodiment of the invention. The method comprises monitoring an electrical current supplied to the collector cell, removing electrical power to the collector cell if the electrical current exceeds a predetermined cell current threshold for a predetermined time period, and generating an indication if the electrical power is removed from the collector cell. The method further comprises restoring the electrical power to the collector cell upon a power cycle, monitoring the electrical current, and removing the electrical power to the collector cell and generating the indication if the electrical current exceeds the predetermined cell current threshold for the predetermined time period after restoring the electrical power.

BRIEF DESCRIPTION OF THE DRAWINGS

The same reference number represents the same element on all drawings. It should be noted that the drawings are not necessarily to scale.

DETAILED DESCRIPTION OF THE INVENTION

FIGS. 1-6 and the following descriptions depict specific embodiments to teach those skilled in the art how to make and use the best mode of the invention. For the purpose of teaching inventive principles, some conventional aspects have been simplified or omitted. Those skilled in the art will appreciate variations from these embodiments that fall within the scope of the invention. Those skilled in the art will also appreciate that the features described below can be combined in various ways to form multiple variations of the invention. As a result, the invention is not limited to the specific embodiments described below, but only by the claims and their equivalents.

Figure 1:
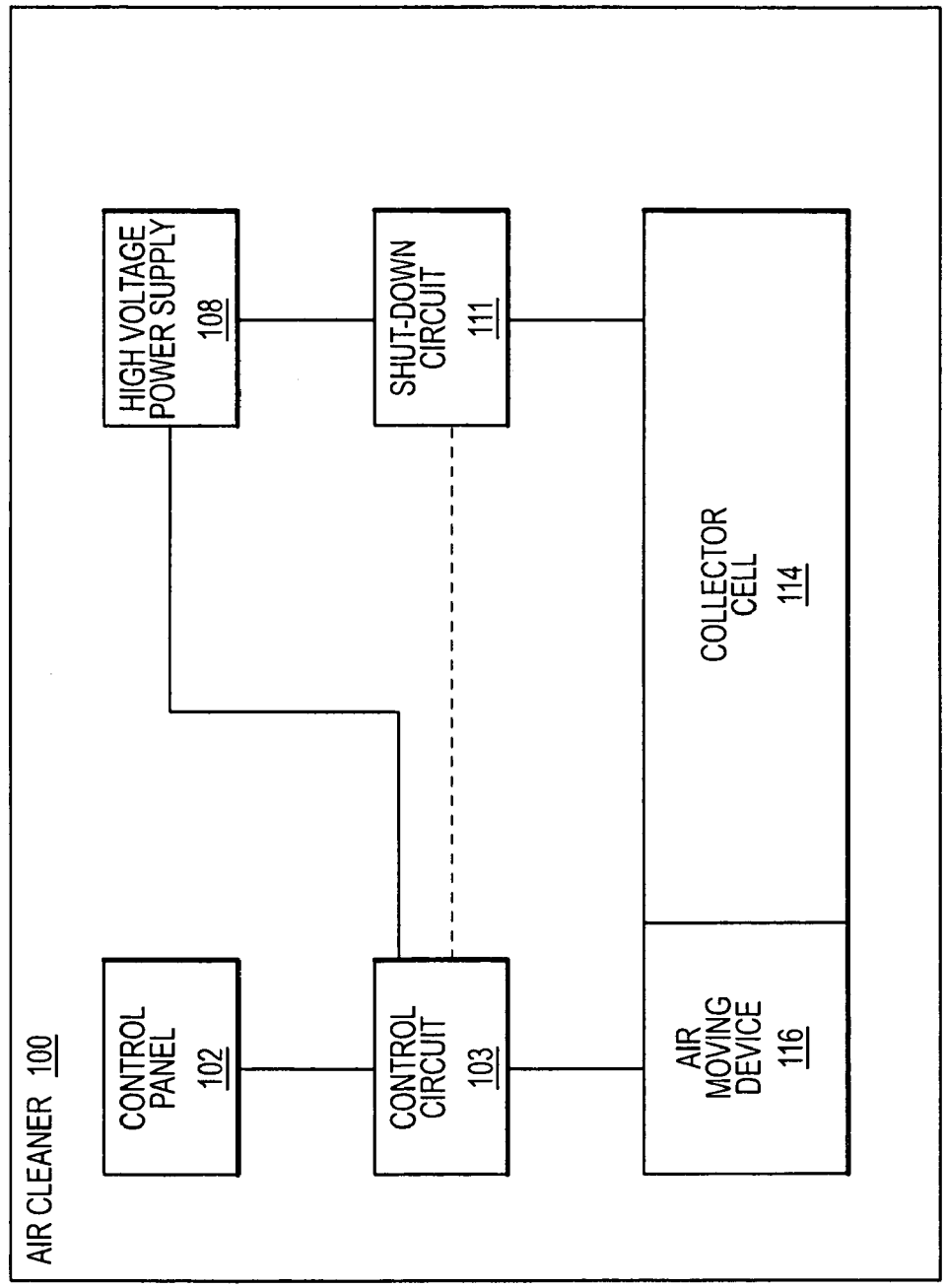
FIG. 1 shows an air cleaner according to an embodiment of the invention.

FIG. 1 shows an air cleaner 100 according to an embodiment of the invention. The air cleaner 100 in the embodiment shown includes a control panel 102, a control circuit 103, a high voltage power supply 108, a shut-down circuit 111, a collector cell 114, and an air moving device 116.

The collector cell 114 removes dirt and debris from the airflow by means of a high voltage electric field. The collector cell 114 can comprise an electrostatic precipitator that includes charged and grounded plates. A high voltage potential across the plates negatively charges particles present in the airflow, wherein the charged particles are attracted to the grounded plates. Alternatively, the collector cell 114 can comprise an ionizer including one or more ionizer wires or other electrodes, wherein particles present in the airflow are negatively charged. The ionizer can comprise one or both of a pre-ionizer or a post-ionizer. The charging of the particles can neutralize or kill living organisms. In addition, the charged particles, after exiting the air cleaner 100, will be attracted to various surfaces around the home and will be pulled out of the air. In another alternative, the collector cell 114 can comprise an electrostatic precipitator combined with an ionizer.

The air moving unit 116 can comprise one or more motors and fans for generating an airflow. The air moving unit 116 can be controlled to generate various levels of airflow through the collector cell 114.

The high voltage power supply 108 generates a direct current (DC) high voltage for the collector cell 114. The voltage is typically on the order of thousands of volts or even tens of thousands of volts.

The control circuit 103 can control overall operation of the air cleaner 100. The control circuit 103 is connected to the control panel 102. The control circuit 103 can receive user inputs through the control panel 102. The control circuit 103 can generate outputs to the control panel 102, such as lighting indicator lights, for example. In addition, in some embodiments the control circuit 103 is connected to the air moving device 116, the high voltage power supply 108, and the shut-down circuit 111. The control circuit 103 in some embodiments can send signals, commands, etc., to these components. The control circuit 103 in some embodiments can receive signals, feedback, or other data from these components. The control circuit 103 in some embodiments is coupled to and communicates with the shut-down circuit 111 (dashed lines).

The shut-down circuit 111 is configured to monitor an electrical current supplied to the collector cell, remove electrical power to the collector cell if the electrical current exceeds a predetermined cell current threshold for a predetermined time period, and generate an indication. The shut-down circuit 111 can be located between the high voltage power supply 108 and the collector cell 114, as shown, wherein the shut-down circuit 111 can interrupt the electrical power that is supplied to the collector cell 114. As a result, the shut-down circuit 111 can make or break the power lines between the high voltage power supply 108 and the collector cell 114. It should be noted that electrical power to the air moving device 116 can be maintained or can be terminated when the electrical power to the collector cell 114 is removed.

After an arc or short has exceeded the predetermined time period, an indication is generated. The indication in one embodiment comprises a light that is illuminated. The indication can include a steady illumination or a blinking illumination. Alternatively, other trouble indications can be generated, including audible signals. The indication is generated until a power cycle of the air cleaner 100 occurs (see FIG. 4 and the accompanying discussion).

Figure 2:
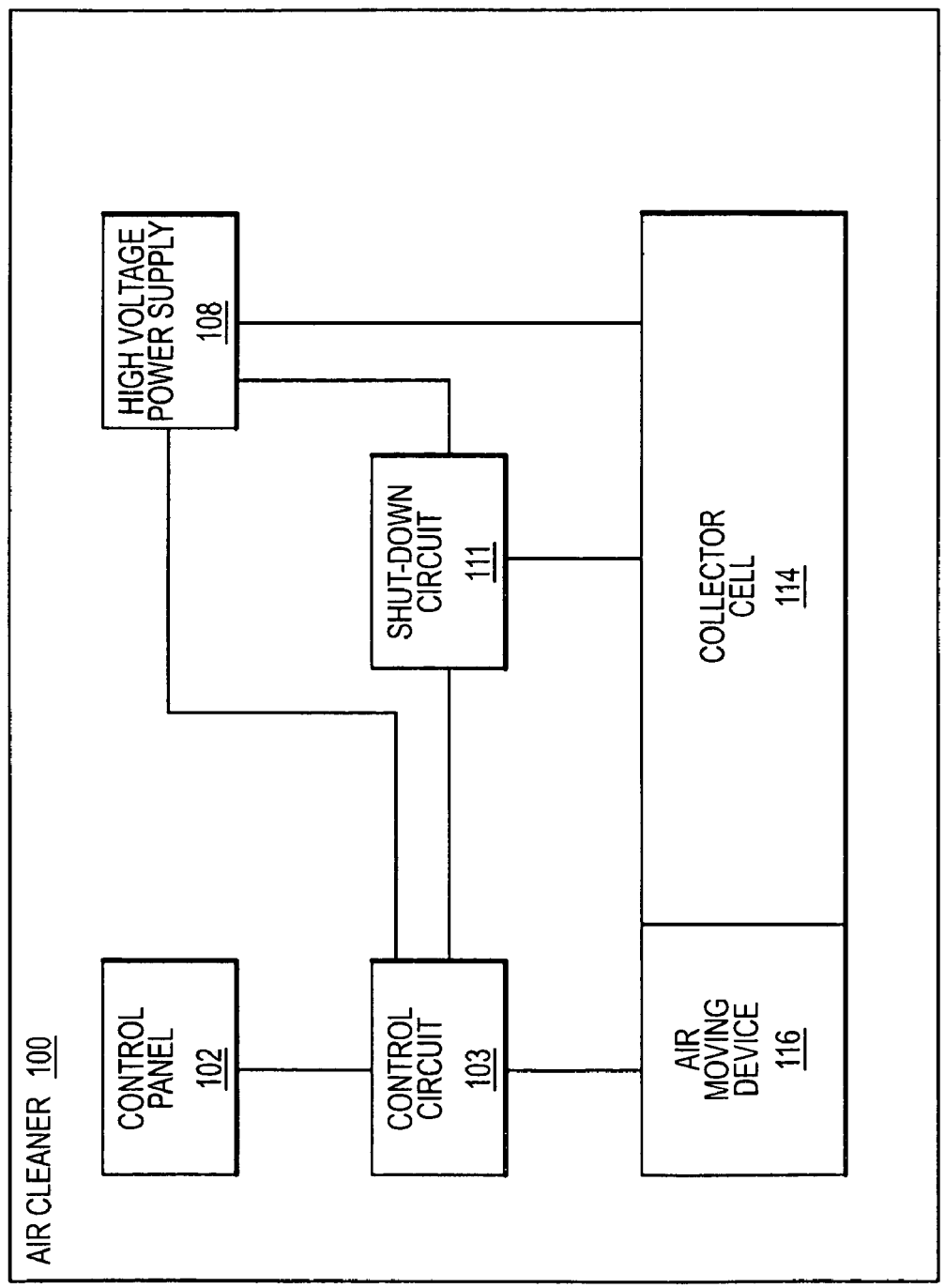
FIG. 2 shows an alternative embodiment of the air cleaner according to the invention.

FIG. 2 shows an alternative embodiment of the air cleaner 100 according to the invention. The shut-down circuit 111 can receive a voltage level measurement from the high voltage power supply 108, from the control circuit 103, or from the collector cell 114. In this embodiment, the shut-down circuit 111 can send a message, command, or signal to the high voltage power supply 108, wherein the high voltage power supply 108 terminates the supply of electrical power to the collector cell 114. The shut-down circuit 111 does not directly interrupt the electrical power.

Figure 3:
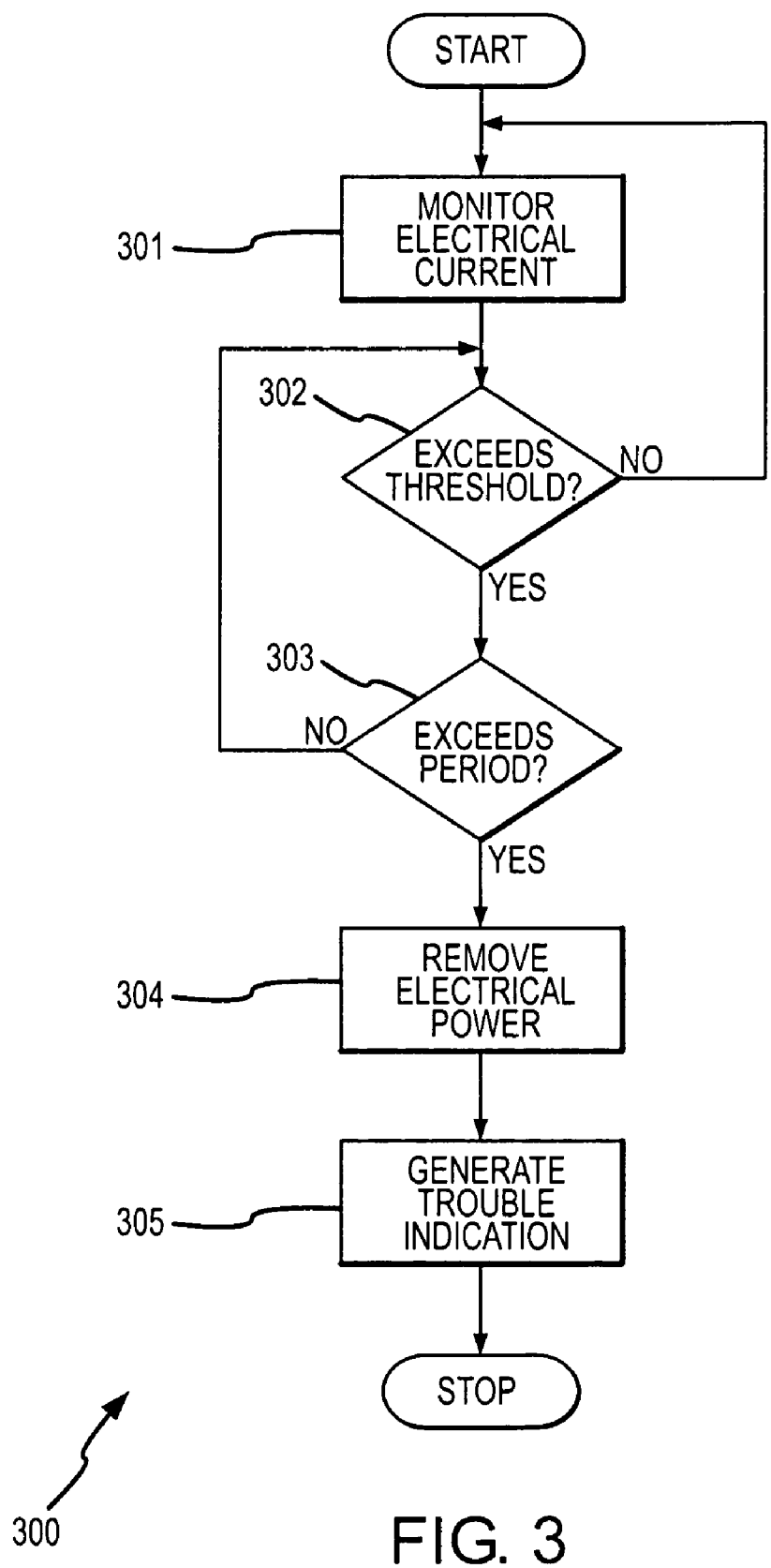
FIG. 3 is a flowchart of a shut-down method for a collector cell of the air cleaner according to an embodiment of the invention.

FIG. 3 is a flowchart 300 of a shut-down method for the collector cell 114 of the air cleaner 100 according to an embodiment of the invention. In step 301, the electrical current being supplied to the collector cell 114 is monitored. For example, the electrical current can be compared to a predetermined current threshold. The predetermined current threshold can designate a current level that is determined to be above a normal, expected, or safe current draw.

In step 302, if the electrical current exceeds the predetermined current threshold, then the method proceeds to step 303. Otherwise, if the electrical current does not exceed the predetermined current threshold, then the method loops back to step 301.

In step 303, if a predetermined time period is exceed, then the method proceeds to step 304. Otherwise, the method branches back to step 302 and waits. The predetermined time period comprises a time period for which the current must exceed the threshold before the shut-down is activated. This is done in order to overlook temporary current spikes, such as current draws due to substantially momentary arcing or popping in the collector cell. The predetermined time period can comprise several seconds, for example. However, other time periods are contemplated and are within the scope of the description and claims.

In step 304, because the electrical current has exceeded the predetermined current threshold for the predetermined time period, the electrical power is removed from the collector cell 114.

In step 305, an indication is generated. The indication can comprise any manner of visual indication presented to a user or operator of the air cleaner. For example, a check collector cell indicator light 131 can be activated (see FIGS. 5-6 and the accompanying text below).

Figure 4:
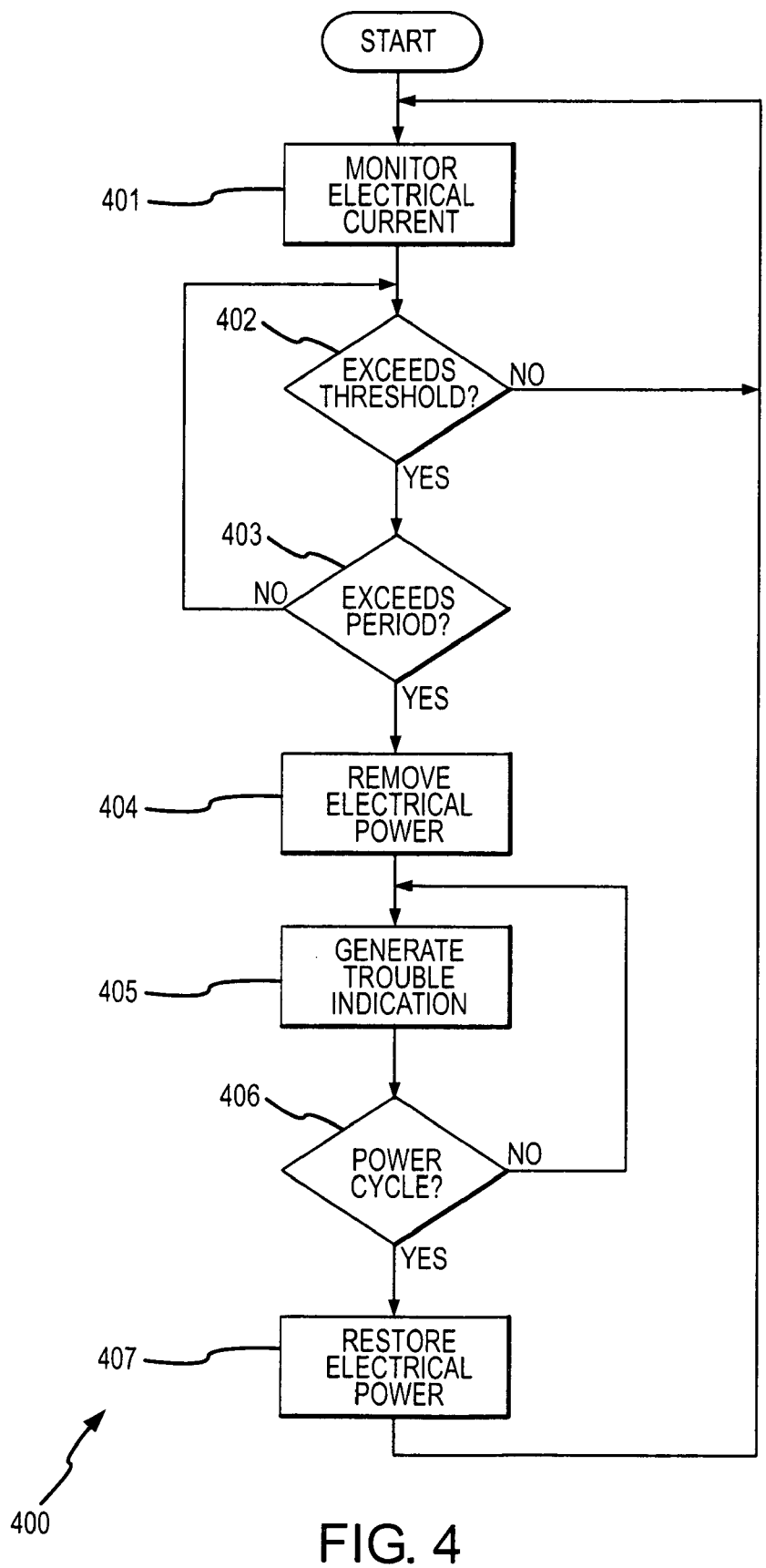
FIG. 4 is a flowchart of a shut-down method for the collector cell of the air cleaner according to an embodiment of the invention.

FIG. 4 is a flowchart 400 of a shut-down method for the collector cell 114 of the air cleaner 100 according to an embodiment of the invention. In step 401, the electrical current being supplied to the collector cell 114 is monitored, as previously discussed.

In step 402, if the electrical current exceeds the predetermined current threshold, then the method proceeds to step 403. Otherwise, if the electrical current does not exceed the predetermined current threshold, then the method loops back to step 401, as previously discussed.

In step 403, if a predetermined time period is exceeded, then the method proceeds to step 404. Otherwise, the method branches back to step 402 and waits the predetermined time period, as previously discussed.

In step 404, because the electrical current has exceeded the predetermined current threshold for the predetermined time period, the electrical power is removed from the collector cell 114, as previously discussed.

In step 405, an indication is generated, as previously discussed.

In step 406, if a power cycle has occurred, then the method proceeds to step 407. Otherwise, the method loops back to step 405 and waits for a power cycle. Consequently, the indication is generated until a power cycle of the air cleaner 100 occurs. In addition, the electrical power is not restored.

Figure 5:
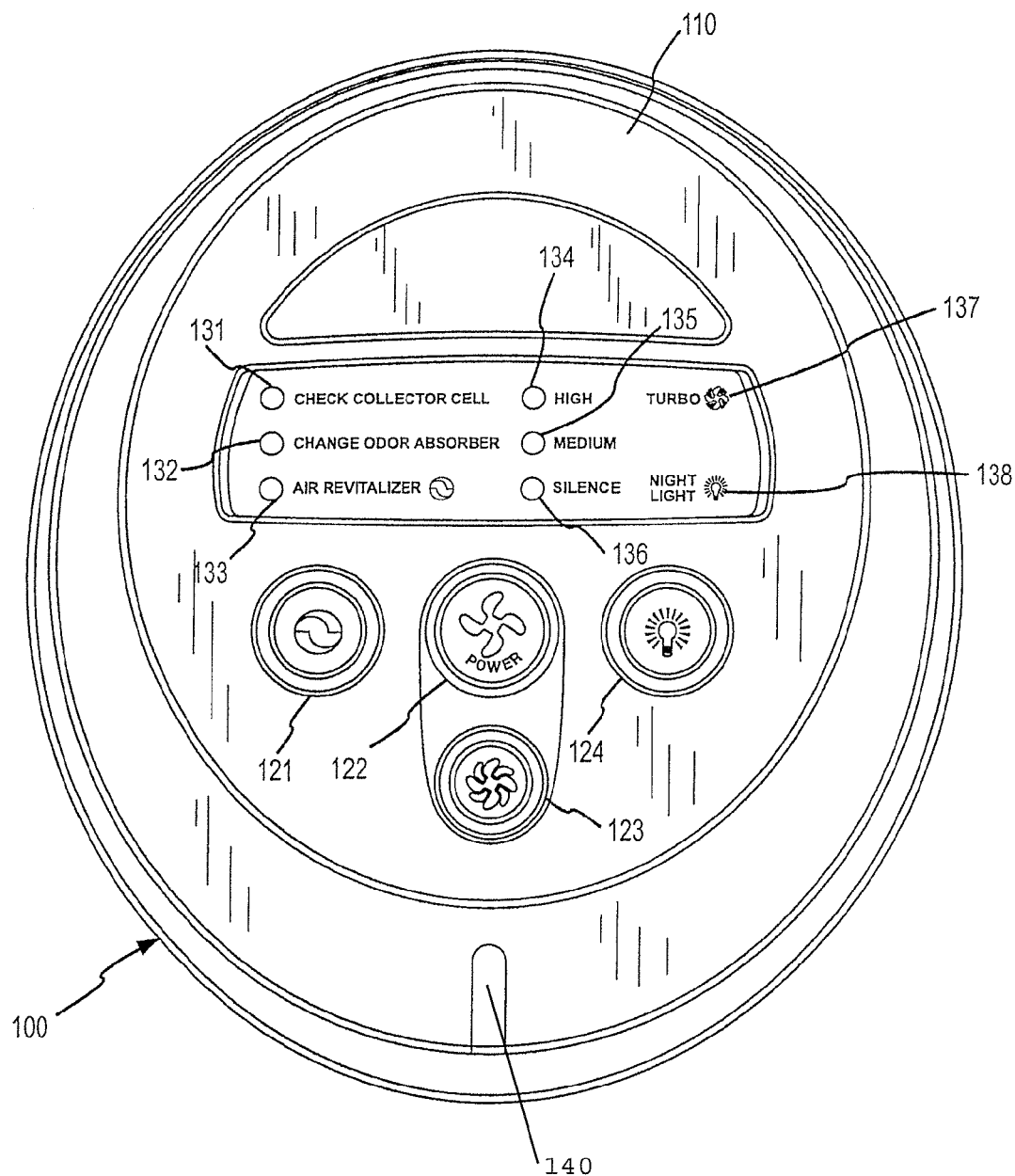
FIG. 5 shows detail of a control panel of the air cleaner according to an embodiment of the invention.
Figure 6:
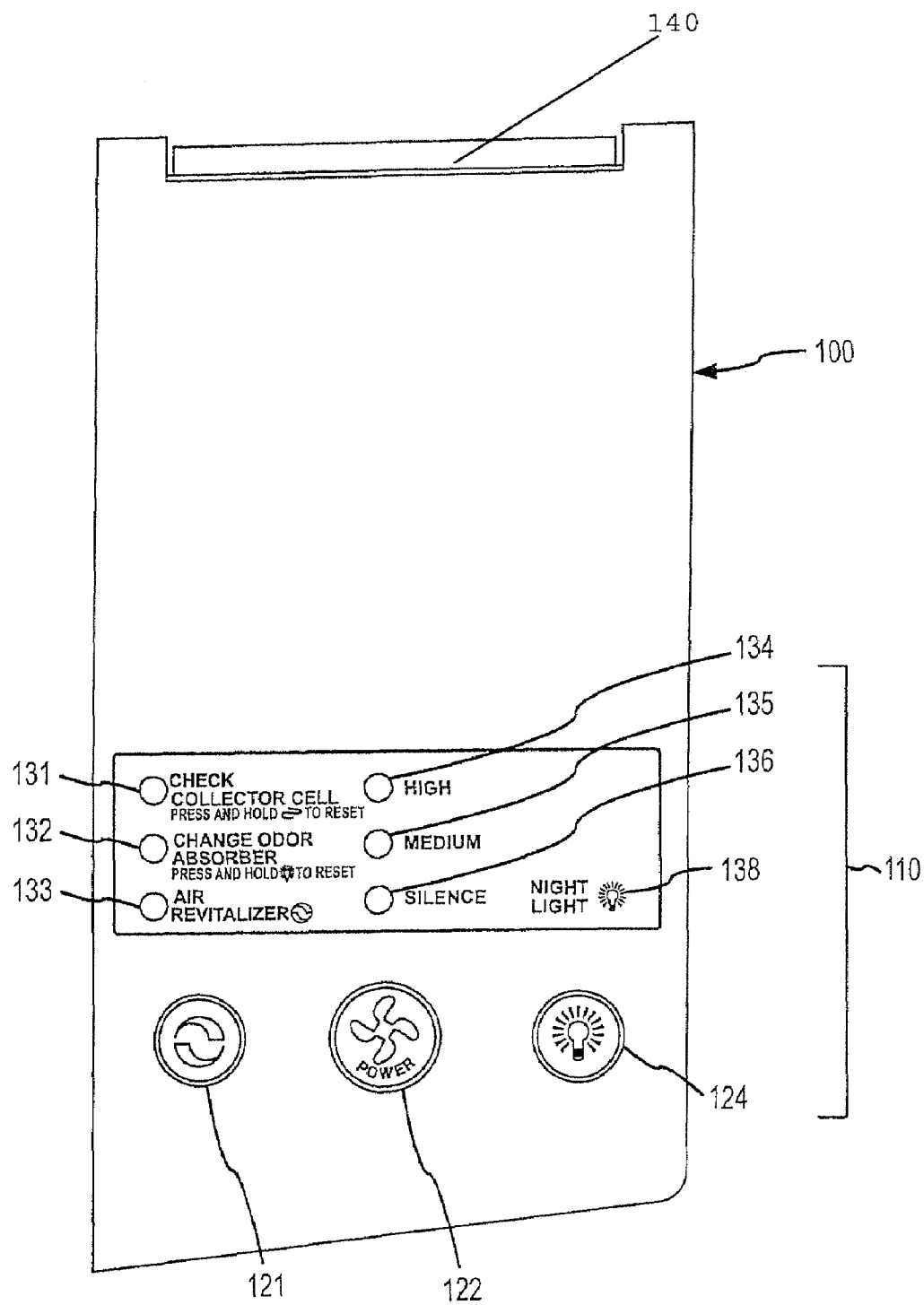
FIG. 6 shows the control panel according to another embodiment of the invention.

The power cycle can comprise a person pressing the power button 122 (see FIGS. 5-6). In addition or alternatively, the power cycle can comprise a person unplugging the air cleaner 100 from a power outlet. Other power cycle actions are contemplated and are within the scope of the description and claims.

In step 407, because a power cycle has occurred, electrical power is restored to the collector cell 114. The collector cell 114 therefore resumes operation. In addition, the indication is terminated.

The original cause of the shut-down may or may not have been removed before the power cycle. If the shut-down cause has been removed, such as by cleaning the collector cell 114, then the collector cell 114 will operate normally. For example, the collector cell 114 can be shut-down because of excessive moisture due to a washing operation, wherein the collector cell 114 may subsequently dry out by the time a power cycle occurs.

Alternatively, if the shut-down cause has not been removed, then the shut-down circuit 111 may again remove electrical power from the collector cell 114, after the predetermined time period has again expired. However, restoration of the electrical power may burn up any cause or causes of the original shut down. For example, any arcing or shorting that again occurs after the restoration of electrical power may burn up obstructions, dirt, or build-up in the collector cell 114. Therefore, it is advantageous to restore electrical power after a power cycle, even if the restoration is only momentary.

FIG. 5 shows detail of a control panel 110 of the air cleaner 100 according to an embodiment of the invention. The control panel 110 includes various controls, including an air revitalizer (i.e., ionizer) button 121, a fan power button 122, a fan turbo button 123, and a nightlight button 124. Other controls are contemplated and are within the scope of the description and claims. In addition, other control types, such as sliders, switches, touch sensors, optical sensors, etc., are contemplated and are within the scope of the description and claims.

Pressing the air revitalizer button 121 turns the air revitalizer on and off. Pressing the fan power button 122 cycles the fan of the air cleaner 100 through the fan power levels. To turn the air cleaner 100 on, the user presses the fan power button 122 once. Power comes on in the low i.e., "silence" setting. Subsequent presses of the fan power button 122 transitions the fan to the medium speed, to the high speed, and then turns the fan off. The electrostatic precipitator cell is turned on when the fan is running at any speed. Pressing the fan turbo button 123 runs the fan at its highest speed, the turbo speed. This speed setting is accompanied by illumination of the turbo fan speed indicator 137. The electrostatic precipitator is on when the fan is at the turbo speed setting. The turbo speed setting can be turned off by a subsequent press of the fan turbo button 123 or by cycling off the power of the air cleaner 100, for example.

The control panel further includes various visual indicators, including a check collector cell indicator 131, a change odor absorber indicator 132, an air revitalizer indicator 133, a high fan speed indicator 134, a medium fan speed indicator 135, a silence fan speed indicator 136, a turbo fan speed indicator 137, and a nightlight indicator 138.

The check collector cell indicator 131 is generally illuminated when a collector cell (i.e., electrostatic precipitator) of the air cleaner 100 is dirty and requires cleaning. The collector cell may require cleaning after a predetermined number of hours of operation, for example. The check collector cell indicator 131 can be illuminated when a corresponding collector cell timer indicates that a predetermined time period has elapsed. In addition, the check collector cell indicator 131 can be illuminated when an arc or short exceeding the predetermined time period has been detected.

The change odor absorber indicator 132 is generally illuminated when an odor absorber requires replacement. The odor absorber may require replacement when an odor absorber material has been consumed or effectively clogged up. The change odor absorber indicator 132 can be illuminated when a corresponding odor absorber timer indicates that a predetermined time period has elapsed.

The air revitalizer indicator 133 is generally illuminated when the air revitalizer (i.e., air ionizer) is operating and ionizing airflow through the air cleaner 100. The air revitalizer indicator 133 is correspondingly turned on and off when the air revitalizer is turned on and off.

The high fan speed indicator 134 is generally illuminated during a high fan output setting. The high indicator 134 is correspondingly turned on and off when the high fan output setting is turned on and off.

The medium fan speed indicator 135 is generally illuminated during a medium fan output setting. The medium indicator 135 is correspondingly turned on and off when the medium fan output setting is turned on and off.

The silence fan speed indicator 136 is generally illuminated during a lowest fan output setting. The silence mode of the air cleaner 100 is therefore relatively quiet. The silence fan speed indicator 136 is correspondingly turned on and off when the silence fan output setting is turned on and off.

The turbo fan speed indicator 137 is generally illuminated during turbo mode operation of a fan motor (or motors). The turbo mode is a highest fan output setting. In some embodiments, the turbo mode is automatically controlled by the air cleaner 100, and cannot be activated by a person. The turbo fan speed indicator 137 is correspondingly turned on and off when the turbo fan output setting is turned on and off.

The nightlight indicator 138 is generally illuminated when a nightlight 140 (see below) is activated. The nightlight indicator 138 is correspondingly turned on and off when the nightlight 140 is turned on and off.

The air cleaner 100 further includes a nightlight 140. The nightlight 140 in the embodiment shown is substantially adjacent to the control panel 110. The nightlight 140 in some embodiments is substantially elongate in shape, as shown. However, it should be understood that the nightlight 140 can comprise any shape and size. The nightlight 140 can perform as a typical nightlight. The nightlight 140 generates light and at least partially illuminates a surrounding area. The nightlight 140 can further illuminate the control panel 110 and enable a person to find the buttons at night. When the nightlight button 124 is pushed, the nightlight 140 is turned on. In addition, the nightlight indicator 138 is illuminated. A subsequent press of the nightlight button 124 turns off the nightlight 140 and the nightlight indicator 138.

FIG. 6 shows the control panel 110 according to another embodiment of the invention. In this embodiment, the air cleaner 100 does not include a fan turbo feature. As before, the check collector cell indicator 131 can be illuminated when an arc or short has been detected and the arc or short has exceeded the predetermined time period. The check collector cell indicator 131 can be steadily illuminated or can be blinking. The check collector cell indicator 131 can be illuminated until a subsequent power cycle occurs.

What is claimed is:

1. A shut-down method for a collector cell of an air cleaner, the method comprising:
   monitoring an electrical current supplied to the collector cell;
   removing electrical power to the collector cell if the electrical current exceeds a predetermined cell current threshold for a predetermined time period; and
   generating an indication if the electrical power is removed from the collector cell.

2. The method of claim 1, with the collector cell comprising an ionizer.

3. The method of claim 1, with the collector cell comprising an electrostatic precipitator.

4. The method of claim 1, with the collector cell comprising an electrostatic precipitator in combination with an ionizer.

5. The method of claim 1, further comprising an air moving device and wherein electrical power to the air moving device is maintained when the electrical power to the collector cell is removed.

6. The method of claim 1, with generating the indication comprising illuminating a check collector cell indicator.

7. The method of claim 1, with generating the indication comprising blinking a check collector cell indicator.

8. The method of claim 1, further comprising:
   restoring the electrical power to the collector cell upon a power cycle; and
   monitoring the electrical current and removing electrical power to the collector cell if the electrical current exceeds a predetermined cell current threshold for a predetermined time period after restoring the electrical power.

9. The method of claim 1, further comprising providing electrical power to an air moving device.

10. A shut-down method for a collector cell of an air cleaner, the method comprising:
    monitoring an electrical current supplied to the collector cell;
    removing electrical power to the collector cell if the electrical current exceeds a predetermined cell current threshold for a predetermined time period;
    generating an indication if the electrical power is removed from the collector cell;
    restoring the electrical power to the collector cell upon a power cycle;
    monitoring the electrical current; and
    removing the electrical power to the collector cell and generating the indication if the electrical current exceeds the predetermined cell current threshold for the predetermined time period after restoring the electrical power.

11. The method of claim 10, with the collector cell comprising an ionizer.

12. The method of claim 10, with the collector cell comprising an electrostatic precipitator.

13. The method of claim 10, with the collector cell comprising an electrostatic precipitator in combination with an ionizer.

14. The method of claim 10, further comprising an air moving device and wherein electrical power to the air moving device is maintained when the electrical power to the collector cell is removed.

15. The method of claim 10, with generating the indication comprising illuminating a check collector cell indicator.

16. The method of claim 10, with generating the indication comprising blinking a check collector cell indicator.

17. The method of claim 10, further comprising providing electrical power to an air moving device.

* * * * *

UNITED STATES PATENT AND TRADEMARK OFFICE
CERTIFICATE OF CORRECTION

PATENT NO. : 7,625,424 B2  
APPLICATION NO. : 11/500816  
DATED : December 1, 2009  
INVENTOR(S) : Kiern et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 499 days.

Signed and Sealed this

Twenty-sixth Day of October, 2010

David J. Kappos  
*Director of the United States Patent and Trademark Office*